(12) United States Patent
Cui et al.

(10) Patent No.: US 12,169,258 B2
(45) Date of Patent: Dec. 17, 2024

(54) ULTRASONIC IMAGING APPARATUS AND ULTRASONIC IMAGING METHOD

(71) Applicant: BOE TECHNOLOGY GROUP CO., LTD., Beijing (CN)

(72) Inventors: Liang Cui, Beijing (CN); Xue Dong, Beijing (CN); Lei Wang, Beijing (CN); Yangbing Li, Beijing (CN); Yingzi Wang, Beijing (CN); Yanling Han, Beijing (CN); Yubo Wang, Beijing (CN); Yue Gou, Beijing (CN)

(73) Assignee: Beijing BOE Technology Development Co., Ltd., Beijing (CN)

( * ) Notice: Subject to any disclaimer, the term of this patent is extended or adjusted under 35 U.S.C. 154(b) by 0 days.

(21) Appl. No.: 17/778,119

(22) PCT Filed: Jun. 7, 2021

(86) PCT No.: PCT/CN2021/098641
§ 371 (c)(1),
(2) Date: May 19, 2022

(87) PCT Pub. No.: WO2022/256970
PCT Pub. Date: Dec. 15, 2022

(65) Prior Publication Data
US 2024/0168143 A1    May 23, 2024

(51) Int. Cl.
*G01S 7/52* (2006.01)
*A61B 8/14* (2006.01)
*A61B 8/00* (2006.01)

(52) U.S. Cl.
CPC ........... *G01S 7/52019* (2013.01); *A61B 8/145* (2013.01); *A61B 8/54* (2013.01)

(58) Field of Classification Search
CPC .. A61B 8/08; A61B 8/00; A61B 8/145; A61B 8/54; G01S 7/52019;
(Continued)

(56) References Cited

U.S. PATENT DOCUMENTS

| 8,007,439 | B2 * | 8/2011 | Specht | ................. | A61B 8/4209 |
| | | | | | 600/463 |
| 9,986,975 | B2 * | 6/2018 | Specht | ................. | A61B 8/5246 |

(Continued)

*Primary Examiner* — Daniel L Murphy
*Assistant Examiner* — Amie M Ndure
(74) *Attorney, Agent, or Firm* — HOUTTEMAN LAW LLC

(57) ABSTRACT

The present disclosure provides an ultrasonic imaging method and apparatus. The apparatus includes an ultrasonic signal emission source and a receiving array including ultrasonic signal receiving circuits; the method includes: turning on the source to perform emission of ultrasonic waves toward an object to be detected and causing the ultrasonic waves to propagate through the object, a depth-wise direction of which is along a propagation direction of the ultrasonic waves; after a first predetermined time period having elapsed since the source was turned on, turning on the receiving array to receive reflected echoes returning from a first section plane of the object to be detected perpendicular to the depth-wise direction; thereafter, turning off the receiving array, storing the reflected echoes by the ultrasonic signal receiving circuits and acquiring reflected echo signals, and successively reading the reflected echo signals from the ultrasonic signal receiving circuits during a reading time period.

20 Claims, 7 Drawing Sheets

(58) Field of Classification Search
CPC . G01S 15/8915; G01S 7/52085; G16B 30/10; G16B 20/10; G16B 20/20; G16B 30/00
See application file for complete search history.

(56) References Cited

U.S. PATENT DOCUMENTS

| | | | | |
|---|---|---|---|---|
| 2002/0161299 | A1* | 10/2002 | Prater | A61B 8/08 600/443 |
| 2006/0111634 | A1* | 5/2006 | Wu | A61B 8/467 600/443 |
| 2008/0103393 | A1* | 5/2008 | Specht | A61B 8/4209 600/437 |
| 2017/0079621 | A1* | 3/2017 | Specht | G01S 15/8961 |
| 2017/0367686 | A9* | 12/2017 | Specht | G01S 15/8977 |

\* cited by examiner

ULTRASONIC IMAGING APPARATUS AND ULTRASONIC IMAGING METHOD

TECHNICAL FIELD

The present disclosure relates to the technical field of ultrasonic waves, and in particular, to an ultrasonic imaging apparatus and an ultrasonic imaging method.

BACKGROUND

Ultrasonic imaging is to scan a human body using ultrasonic beams and receive and process reflected signals to acquire images of organs in the human body. There are many types of commonly used ultrasonic instruments. An ultrasonic instrument of an amplitude modulation type uses levels of ultrasonic wave amplitudes to indicate strengths of reflected signals and displays an "echo image". An ultrasonic instrument of a bright-spot scanning type displays movement curves of bright spots at different times on a graph whose vertical direction represents shallow to deep locations in a space and whose horizontal direction represents time. As ultrasonic instruments of these two types all display one-dimensional images, their application fields are limited. An ultrasonic instrument of a luminance modulation type, that is, an ultrasonic tomography imaging instrument (also known as a B-mode ultrasonic instrument) indicates strengths of received signals by bright spots with different brightness; as a probe moves along a horizontal direction, the bright spots on a display screen move along the horizontal direction concurrently; and trajectories of these bright spots are joined to form an image of a section plane scanned by ultrasonic beams, thereby obtaining a two-dimensional image.

SUMMARY

The present disclosure provides an ultrasonic imaging apparatus and an imaging method thereof.

The ultrasonic imaging apparatus includes an ultrasonic signal emission source and a receiving array that includes a plurality of ultrasonic signal receiving circuits, both of which define a detection region; the detection region includes a farthest interface, which is an edge interface of the detection region distal to the receiving array; the ultrasonic imaging apparatus is able to detect an object to be detected in the detection region; and the imaging method includes: turning on the ultrasonic signal emission source to perform a first emission of ultrasonic waves toward the detection region and causing the ultrasonic waves to propagate through the detection region, a depth-wise direction of which is along a propagation direction of the ultrasonic waves, and thereafter, turning off the ultrasonic signal emission source; and turning on the receiving array at a first time point after a first predetermined time period having elapsed since the ultrasonic signal emission source was turned on, so as to simultaneously receive a plurality of reflected echoes returning from the detection region by the plurality of ultrasonic signal receiving circuits included in the receiving array, and thereafter, causing the receiving array not to receive any reflected echoes, storing the plurality of reflected echoes by the plurality of ultrasonic signal receiving circuits, acquiring a plurality of reflected echo signals as a plurality of reflected echo signals relating to a first slice in the first emission, and reading the plurality of reflected echo signals relating to the first slice successively from the plurality of ultrasonic signal receiving circuits during a reading time period.

In one embodiment, after the reading the plurality of reflected echo signals successively, the imaging method further includes: turning on the receiving array at a second time point to simultaneously receive a plurality of reflected echoes returning from the detection region by the plurality of ultrasonic signal receiving circuits included in the receiving array, and thereafter, causing the receiving array not to receive any reflected echoes, storing the plurality of reflected echoes by the plurality of ultrasonic signal receiving circuits, acquiring a plurality of reflected echo signals as a plurality of reflected echo signals relating to a second slice in the first emission, and reading the plurality of reflected echo signals relating to the second slice successively from the plurality of ultrasonic signal receiving circuits during a reading time period.

In one embodiment, a time difference between the second time point and the first time point is a reading time of a slice image; and the first predetermined time period is less than or equal to a time length obtained by dividing a sum of a distance between the ultrasonic signal emission source and a surface of the object to be detected and a distance between the surface of the object to be detected and the receiving array by a velocity of the ultrasonic waves.

In one embodiment, after the reading the plurality of reflected echo signals successively, the receiving array is turned on again immediately; and after the reading the plurality of reflected echo signals received and relating to the second slice as a preceding slice successively, the imaging method further includes: step S1: turning on the receiving array again to simultaneously receive a plurality of reflected echoes returning from the detection region by the plurality of ultrasonic signal receiving circuits included in the receiving array, thereafter, storing the plurality of reflected echoes by the plurality of ultrasonic signal receiving circuits and acquiring a plurality of reflected echo signals as a plurality of reflected echo signals relating to a succeeding slice, and thereafter, reading the plurality of reflected echo signals relating to the succeeding slice successively from the plurality of ultrasonic signal receiving circuits during a reading time period; and step S2: repeating the step S1 until the succeeding slice goes beyond the farthest interface of the detection region, and after completing the step S2, acquiring number of turn-on times of the receiving array for the first emission of the ultrasonic signal emission source as number of slices N in a single wavelength.

In one embodiment, a distance between the surface of the detection region and the farthest interface of the detection region is a detection distance s; and when a product of the number of turn-on times of the receiving array and the reading time of the slice image is greater than the detection distance s, it is determined that a slice that has been received goes beyond the farthest interface of the detection region.

In one embodiment, after the succeeding slice going beyond the farthest interface of the detection region, the imaging method further includes step S3: turning on the ultrasonic signal emission source again to perform another emission of ultrasonic waves toward the detection region and causing the ultrasonic waves to propagate through the detection region, the depth-wise direction of which is along the propagation direction of the ultrasonic waves, and thereafter, turning off the ultrasonic signal emission source; turning on the receiving array after a second predetermined time period having elapsed since the ultrasonic signal emission source was turned on again, so as to simultaneously receive a plurality of reflected echoes returning from the detection region by the plurality of ultrasonic signal receiving circuits included in the receiving array, and thereafter, causing the receiving array not to receive any reflected echoes, storing the plurality of reflected echoes by the plurality of ultrasonic signal receiving circuits, acquiring a plurality of reflected echo signals as a plurality of reflected echo signals relating to a first slice in the other emission, and reading the plurality of reflected echo signals relating to the first slice successively from the plurality of ultrasonic signal receiving circuits during a reading time period, wherein the second predetermined time period is longer than the first predetermined time period as a preceding predetermined time period by a predetermined fine-tuning time length.

In one embodiment, a result of the predetermined fine-tuning time length divided by two is greater than or equal to v/f*N and less than the reading time of the slice image, where f is a frequency of the ultrasonic waves, N is the number of slices in a single wavelength and v is the velocity of the ultrasonic waves.

In one embodiment, number of turn-on times of the ultrasonic signal emission source M is equal to one plus a result of the reading time of the slice image divided by the result of the predetermined fine-tuning time length divided by two.

In one embodiment, the imaging method further includes: after the reading the plurality of reflected echo signals relating to the first slice in the other emission successively, turning on the receiving array again; and performing the step S3, the step S1 and the step S2 successively.

In one embodiment, the imaging method further includes integrating the reflected echo signals that have been read to determine information about the object to be detected in the detection region.

The ultrasonic imaging apparatus of the present disclosure includes an ultrasonic signal emission source emitting ultrasonic waves toward an object to be detected; and a receiving array including a plurality of ultrasonic signal receiving circuits, wherein the ultrasonic signal emission source and the receiving array define a detection region and a farthest interface of the detection region, such that the receiving array is able to receive, store and read a plurality of reflected echo signals returning from the object to be detected in the detection region; the ultrasonic signal emission source is a point emission source; the receiving array and the ultrasonic signal emission source are on a first plane; and a depth-wise direction of the detection region is orthogonal to the first plane.

In one embodiment, the ultrasonic signal emission source is directly above the receiving array or on top of the receiving array.

In one embodiment, the ultrasonic signal emission source is at a center of the receiving array.

In one embodiment, an orthographic projection of the detection region on the receiving array falls within the receiving array.

In one embodiment, the plurality of ultrasonic signal receiving circuits are arranged in an array.

In one embodiment, the ultrasonic imaging apparatus further includes a driving circuit, which is connected to the receiving array through a plurality of gate lines and a plurality of reading lines, wherein each of the plurality of gate lines is connected to a row of ultrasonic signal receiving circuits to control the row of ultrasonic signal receiving circuits to be turned on; and each of the plurality of reading lines is connected to a column of ultrasonic signal receiving circuits to read a plurality of reflected echo signals stored in the column of ultrasonic signal receiving circuits.

In one embodiment, each of the plurality of ultrasonic signal receiving circuits includes: an ultrasonic receiver, a first transistor, a second transistor and a third transistor, wherein the ultrasonic receiver includes a driving electrode, a piezoelectric material layer and a receiving electrode, the driving electrode is connected to ground, and the receiving electrode is used to receive the plurality of reflected echo signals; the first transistor includes a control electrode, a first electrode and a second electrode, the control electrode of the first transistor is connected to a reset signal terminal, the first electrode of the first transistor is connected to the receiving electrode, and the second electrode of the first transistor is connected to a bias voltage terminal; the second transistor includes a control electrode, a first electrode and a second electrode, the first electrode of the second transistor is connected to a power supply voltage, and the control electrode of the second transistor is connected to the receiving electrode; and the third transistor includes a control electrode, a first electrode and a second electrode, the first electrode of the third transistor is connected to the second electrode of the second transistor, the control electrode of the third transistor is connected to a corresponding gate line, and the second electrode of the third transistor is connected to a corresponding reading line.

BRIEF DESCRIPTION OF THE DRAWINGS

In order to make various embodiments of the present more clearly, a brief description will be hereinafter given to the drawings relating to these embodiments. Apparently, the drawings to be described below only illustrate some embodiments of the present disclosure, and the present disclosure is not limited thereto.

DETAILED DESCRIPTION OF THE EXEMPLARY EMBODIMENTS

In order to enable a person skilled in the art to better understand the technical solutions of the present disclosure, a detailed description will hereinafter be given to the ultrasonic imaging apparatus and the imaging method thereof provided in the present disclosure with reference to the accompanying drawings and embodiments.

In the related art, ultrasonic imaging is typically to receive echo signals by an array in real time and convert time information and amplitude values of the echo signals into gray-scale values for display. Since a velocity of ultrasonic waves is low, this imaging method requires receiving all echoes returning from a distance, one emission of ultrasonic waves only generates one image of an elongated region of an object to be detected, and the process is repeated many times in order to synthesize a complete image of the object to be detected, thereby taking up a great deal of time and thus resulting in a low frame transmission rate of image and poor display effect.

To solve this problem, the present disclosure provides an ultrasonic imaging apparatus and an imaging method thereof.

Figure 1A:
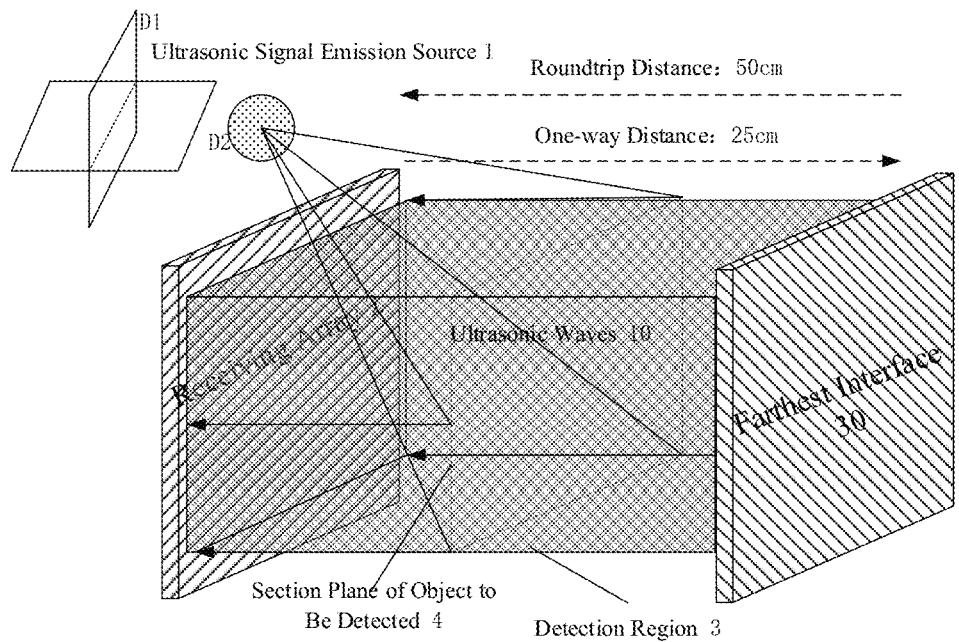
FIG. 1A is a schematic diagram of a structure of an ultrasonic imaging apparatus according to some embodiments of the present disclosure.
Figure 1B:
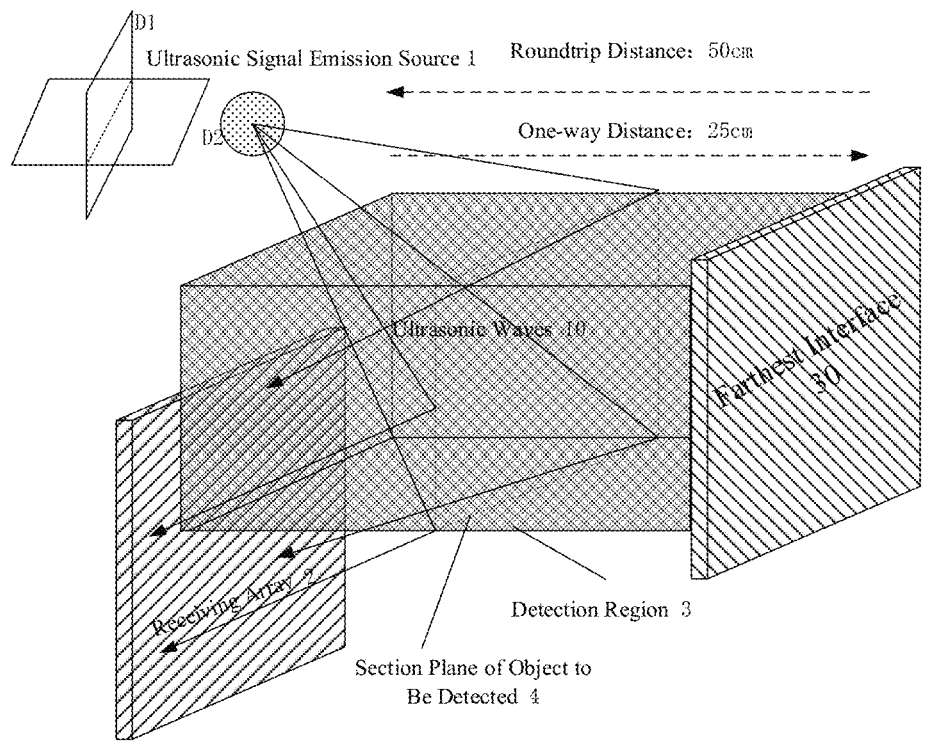
FIG. 1B is a schematic diagram of a structure of an ultrasonic imaging apparatus according to some embodiments of the present disclosure.
Figure 4:
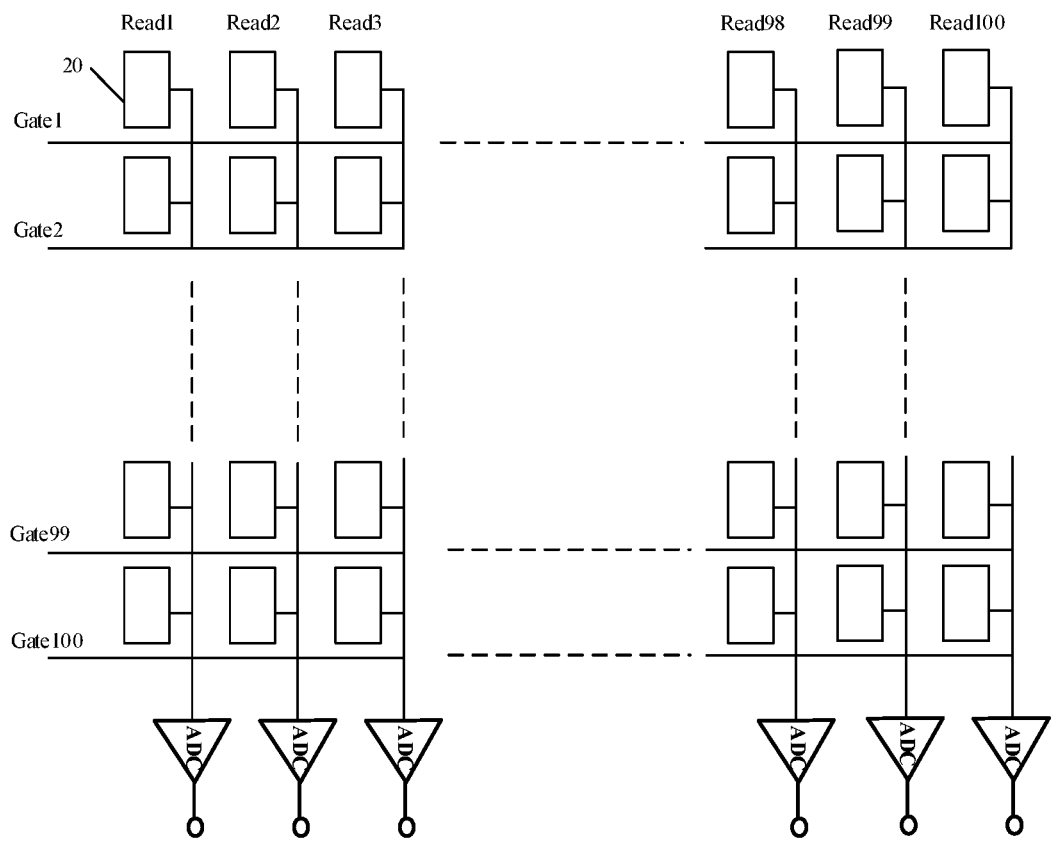
FIG. 4 is a schematic diagram of a receiving array of an ultrasonic imaging apparatus according to some embodiments of the present disclosure.

As shown in FIGS. 1A and 1B, the ultrasonic imaging apparatus of the present disclosure includes: an ultrasonic signal emission source 1 emitting ultrasonic waves 10 to an object to be detected; and a receiving array 2 including a plurality ultrasonic signal receiving circuits 20, for example, a plurality of ultrasonic receiving circuits 20 arranged in an array as shown in FIG. 4, which are used to simultaneously receive a plurality of reflected echoes returning from a section plane 4 of the object to be detected in a detection region 3 and are therefore able to generate a plurality of reflected echo signals corresponding to the plurality of reflected echoes. The ultrasonic signal emission source 1 and the receiving array 2 may be combined to define the detection region 3 and a farthest interface 30 thereof, such that the receiving array is able to receive, store and read the reflected echo signals returning from the object to be detected in the detection region 3, wherein the farthest interface 30 is an edge interface of the detection region 3 distal to the receiving array 2. In other words, the ultrasonic imaging apparatus including the ultrasonic signal emission source 1 and the receiving array 2 is able to detect the object to be detected in the detection region 3. For example, as shown in FIG. 1, the ultrasonic waves 10 reach the section plane 4 of the object to be detected in the detection region 3; and the reflected echoes returning from the object to be detected propagate toward the receiving array 2 and are received, stored and read by the receiving array 2, whereby information about the section plane 4 of the object to be detected can be acquired. The detection region 3 defines the farthest interface 30, and an object to be detected beyond the farthest interface 30 will not be detected. For example, as shown in FIG. 1, an upper limit of a detection distance of the ultrasonic imaging apparatus is around 25 cm, that is, a distance from the farthest interface 30 to the receiving array 2 is around 25 cm.

The ultrasonic signal emission source 1 and the receiving array 2 with specific parameters may be selected according to detection requirements for the detection region 3 and the farthest interface 30, and are not limited herein.

In some embodiments of the present disclosure, the ultrasonic signal emission source 1 may be a point emission source, which will emit spherical waves after being turned on, such that all objects to be detected within a predetermined distance around it (e.g., a distance from the farthest interface 30 to it) may receive the spherical ultrasonic waves; after a surface of the object to be detected reflects the ultrasonic waves, the receiving array 2 receives the reflected echoes, thereby acquiring information about the surface thereof.

In some embodiments shown in FIG. 1A, the ultrasonic signal emission source 1 and the receiving array 2 are on a first plane D1; the detection region 3 may be determined by adjusting the relative positions of the ultrasonic signal emission source 1 and the receiving array 2, for example, the detection region 3 and the receiving array 2 may be on a second plane D2, which intersects with the first plane D1. In one embodiment, the first plane D1 may be orthogonal to the second plane D2, and in such case, a depth-wise direction of the detection region 3 may be regarded as being orthogonal to the first plane D1. With the arrangement as described above, almost all the echoes reflected by the section plane 4 of the object to be detected in the detection region 3 can be received by the receiving array 4 simply by controlling a distance from the ultrasonic signal emission source 1 to the receiving array 2 and an angle between an emitting ultrasonic wave and a receiving ultrasonic wave, thereby improving the detection accuracy. For example, the distance from the ultrasonic signal emission source 1 to the receiving array 2 and the angle between the emitting ultrasonic wave and the receiving ultrasonic wave may be further arranged such that the echoes reflected by the object to be detected in the detection region 3 are incident on the receiving array 2 at an angle perpendicular to the receiving array 2, and this arrangement can increase amplitudes of detection signals as well as detection resolution and sensitivity.

For example, as shown in FIG. 1A, the ultrasonic signal emission source 1 is directly above the receiving array 1, and ultrasonic waves emitted by it are irradiated on and then reflected by the section plane 4 of the object to be detected; and all the reflected echo signals are irradiated toward the receiving array 2 approximately at the angle perpendicular to the receiving array 2 and along the depth-wise direction of the detection region 3, and these signals are stored and read by the receiving array 2 to acquire information about the section plane 4 of the object to be detected. In other words, in this embodiment, an orthographic projection of the detection region 3 on the receiving array 2 falls within the receiving array 2. When the ultrasonic signal emission source 1, as shown in FIG. 1, is arranged directly above the receiving array 2, the ultrasonic waves emitted by the ultrasonic signal emission source 1 are spherical waves, and if the object to be detected in the detention region is an object of homogeneous composition, the section plane of the object to be detected simultaneously reflecting the spherical waves may be a sphere. However, the present disclosure is not limited thereto, and the ultrasonic signal emission source 1 and the receiving array 2 together may be arranged at one side of the surface of the object to be detected; for example, they may be arranged at both sides of a perpendicular bisector of the surface of the object to be detected, respectively, or may be arranged at both sides of the perpendicular bisector symmetrically, as shown in FIG. 1B. Furthermore, respective positions of the ultrasonic signal emission source 1 and the receiving array 2 may be configured to be adjustable according to test requirements. The object to be detected is usually not an object of homogenous composition, for example, it may be an organ in the human body, and in such case, a section plane of the object to be detected imaged by a plurality of reflected echo signals simultaneously received by the receiving array 2 may be an irregular sphere rather than the sphere as described above.

In one embodiment of the present disclosure, as shown in FIG. 1A, the ultrasonic signal emission source 1 and the receiving array 2 are on the first plane D1, and the receiving array 2 and the object to be detected 3 may be regarded as being on the second plane D2. Spherical ultrasonic waves simultaneously emitted by the ultrasonic signal emission source 1 as a point emission source will pass through the object to be detected along a propagation direction of the ultrasonic waves. In the present disclosure, a direction along which the ultrasonic waves successively pass through various parts of the object to be detected may be regarded as the depth-wise direction of the object to be detected, that is, the propagation direction of the ultrasonic waves is consistent with the depth-wise direction of the object to be detected.

In order to increase the frame transmission rate of image and to enhance the display effect, the present disclosure provides an ultrasonic imaging method for the ultrasonic imaging apparatus shown in FIG. 1A.

As describe above, in one embodiment of the present disclosure, the ultrasonic signal emission source used in the ultrasonic imaging apparatus is a point emission source, and the ultrasonic waves emitted by it is spherical waves. Echoes reflected by various parts of the object to be detected will reach the receiving array 4 along the propagation direction of the ultrasonic waves, and be received, stored and read by the plurality of ultrasonic signal receiving circuits in the receiving array 4. After the entire receiving array 2 simultaneously receives the reflected echo signals, the receiving array 2 stops receiving reflected echoes, because the receiving array 2 needs to read the plurality of reflected echo signals stored therein in a predetermined reading time period. For example, the length of the predetermined reading time period is decided by the product of the number of rows of ultrasonic signal receiving circuits in the receiving array and a reading time of the reflected echo signals stored in each row. Therefore, after the entire receiving array 2 receives the reflected echo signals, it temporarily stops receiving reflected echoes, and instead, it reads the plurality of reflected echo signals stored therein successively; thereafter, the receiving array 2 is turned on again to receive reflected echo signals. During the process of successively reading the reflected echo signals stored in the ultrasonic signal receiving circuits, ultrasonic waves irradiating toward the object to be detected continue to propagate; therefore, a section plane of the object to be detected imaged by a set of reflected echo signals received by the receiving array 2 after a predetermined reading time is further away from the receiving array 2 by a predetermined distance than the preceding section plane imaged by the set of reflected echo signals received by it last time. Characteristics of various parts of the object to be detected are not homogeneous, for example, in a case where an arm is detected using ultrasonic waves, the speed at which the ultrasonic waves propagate varies depending on whether or not bones exist at locations through which they pass. Accordingly, the respective section planes imaged by the two sets of reflected echo signals (hereinafter referred to slices) received by the entire receiving array 2 one after another may not be regular spheres, but this does not affect the use of the reflected echo signals for data collection and analysis.

Figure 2A:
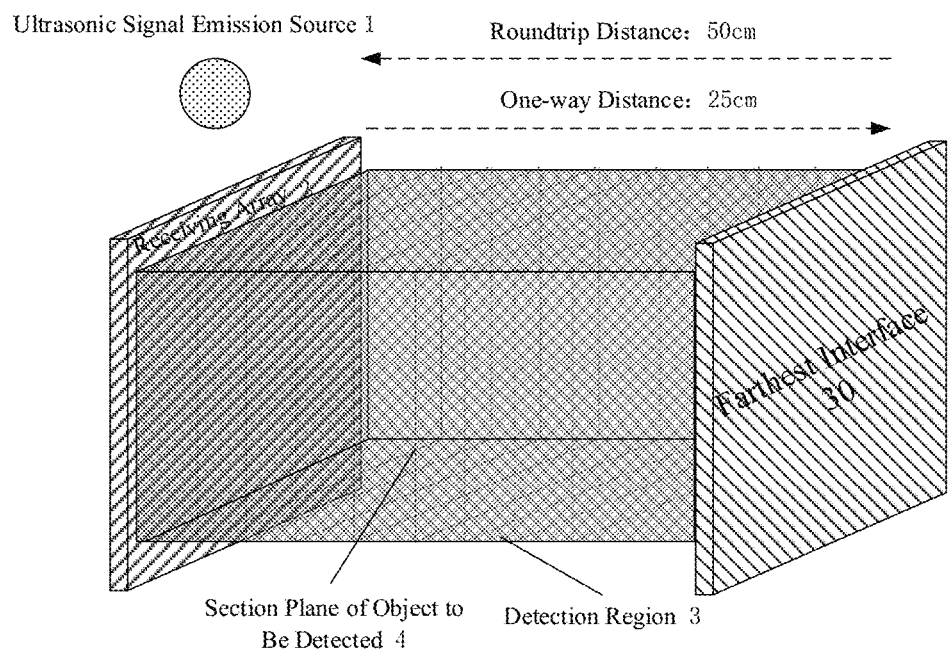
FIG. 2A is a schematic diagram of the slicing of a detection region by an imaging method of an ultrasonic imaging apparatus according to some embodiments of the present disclosure.

For example, as shown in FIG. 2A, the object to be detected is virtually divided into a plurality of slices along the depth-wise direction of the detection region, and the echoes of the ultrasonic waves reflected by section planes of these slices facing the receiving array 2 are received to acquire characteristics of these section planes, which are then integrated to acquire the characteristics of the object to be detected as a whole. Therefore, the larger the number of the divided slices is, the larger the amount of acquired information about the object to be detected will be, and the more accurate the analysis of the object to be detected will be. However, as the number of the slices grows, more time and computation power will be consumed, which may not be beneficial to some types of analysis. Therefore, an appropriate number of slices may be selected according to actual needs.

As described above, in fact, the composition and/or characteristics of various parts of the object to be detected in the detection region 3 are usually not homogeneous. As a result, the echoes of the ultrasonic waves reflected by the section plane of the same slice (e.g., spherical or rectangle slice) of the object to be detected may not reach the receiving array 2 simultaneously, even if various ultrasonic signal receiving circuits in the receiving array 2 are at equal vertical distances to this section plane. Therefore, the plurality of reflected echo signals simultaneously received by the plurality of ultrasonic signal receiving circuits in the receiving array 2 may not necessarily reflect information about the section plane of the same slice of the object to be detected. However, this does not affect the advantage of the ultrasonic imaging method provided in the present disclosure.

It is to be noted that the plurality of slices to be described below approximately correspond to the plurality of virtually divided slices of the object to be detected, and each slice actually represents a set of reflected echo signals simultaneously received by the entire receiving array 2. In a case where the receiving array 2 includes a plurality of ultrasonic signal receiving circuits 20 arranged in an array, a set of reflected echo signals relating to each slice is also arranged in an array.

Figure 2B:
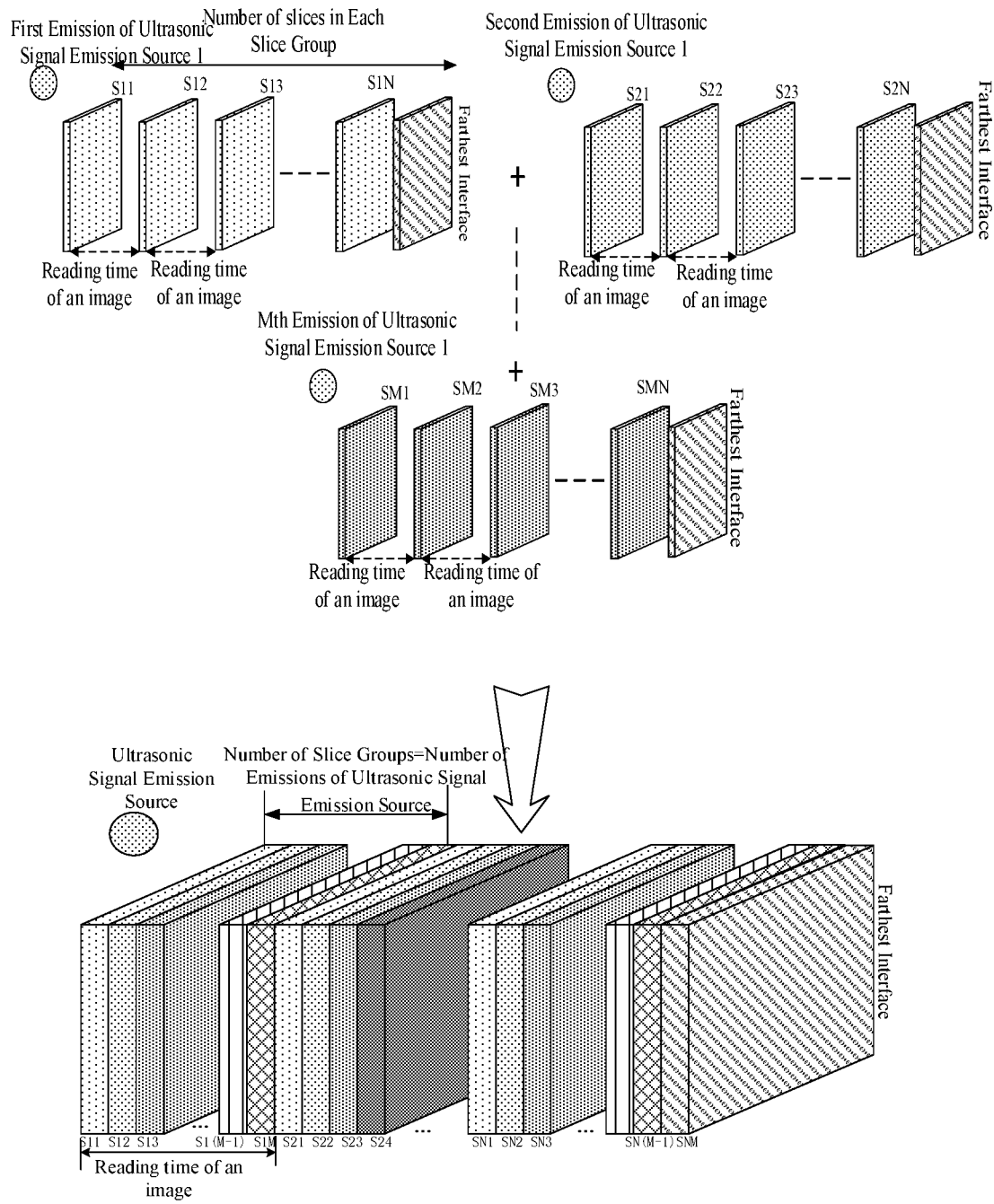
FIG. 2B is a schematic diagram of an imaging method of an ultrasonic imaging apparatus according to some embodiments of the present disclosure.

As shown in FIG. 2B, each time the entire receiving array 2 receives a set of reflected echo signals simultaneously, it needs a certain time to read these signals (that is, a reading time of a slice image shown in FIG. 2). During a first emission of the ultrasonic signal emission source 1, the receiving array 2 receives, stores and reads corresponding sets of reflected echo signals relating to slices S11, S12, S13 . . . S1N successively; these slices reflect information about a specific region in the object to be detected (that is, these slices approximately reflect information about respective section planes of several slices spaced apart from one another in the object to be detected); and a time difference between every two adjacent slices to be read is a reading time of a slice image.

During the first emission of the ultrasonic signal emission source 1, the receiving array 2 first receives a set of echo signals reflected by a section plane of the object to be detected closest to the receiving array 2, that is, receives the slice S11 corresponding to this set of reflected echo signals, as shown in FIG. 2B; after having received the slice 11, the receiving array 2 stops receiving reflected echo signals; after a reading time of a slice image has elapsed, the receiving array 2 is turned on again to receive the slice S12. The above process is repeated until the total receiving time of the reflected echo signals during the first emission exceeds the receiving time of the reflected echo signals returning from the farthest interface.

Then, the ultrasonic signal emission source 1 is turned on for a second emission. During the second emission, the receiving array 2 receives stores and reads corresponding sets of reflected echo signals relating to slices S21, S22, S23

... S2N successively, and each slice reflects characteristics of a specific region of the object to be detected, but information reflected by the reading of the reflected echo signals during the second emission of the ultrasonic signal emission source 1 is different from information about the specific region of the object to be detected acquired during the first emission. There is a short delay time for each of the plurality of slices successively collected during the second emission, compared to those collected during the first emission; and this delay time may be controlled using a time difference between a time when the ultrasonic signal emission source 1 starts one emission and a time when the receiving array 2 is turned on thereafter. Specifically, after the ultrasonic signal emission source 1 started the first emission, the receiving array 2 is turned on after a first predetermined time period has elapsed; and after the ultrasonic signal emission source 1 started the second emission, it is turned on after a second predetermined time period has elapsed, and a difference between the first predetermined time period and the second predetermined time period is a predetermined fine-tuning time, which is equal to the delay time. In other words, a second time difference between a time when the ultrasonic signal emission source 1 starts the second emission and a time when the receiving array is turned on to receive the first slice S21 thereafter may be slightly greater than a first time difference between a time when the ultrasonic signal emission source 1 starts the first emission and a time when the receiving array is turned on to receive the first slice S11 thereafter, but it needs to be ensured that the second time difference does not fall on the collecting time of the second slice S12, that is, a result of the length of the predetermined fine-tune time divided by two is greater than or equal to 1/f*N and less than a reading time of a slice image, where f is a frequency of ultrasonic waves, and N is the number of slices in a single wavelength, which represents the number of slices that can be acquired during one emission of ultrasonic signals; in this way, it can be ensured that information collected during the second emission is not the same information collected during the first emission. In some cases, as shown in FIG. 2B, the division of the detection region needs not to be as precise as that shown in FIG. 2A As shown in FIG. 2B, during the first emission of the ultrasonic signal emission source 1, a time difference between respective receiving times of two consecutive slices, that is, a reading time of a slice image, may be determined in accordance with a time for the receiving array 2 to read a set of reflected echo signals relating to one slice. A transmission distance of the ultrasonic waves within a reading time of a slice image may be obtained by multiplying the reading time of the slice image with the velocity of the ultrasonic waves, and this distance may approximately reflect a distance between two reflective planes of the object to be detected corresponding to two consecutive slices collected during one emission. As shown in FIG. 2B, during the first emission, information about a portion between every two adjacent reflective planes of the object to be detected is not acquired, which may not meet the requirement of the test accuracy. In view of this, in the imaging method of the present disclosure, after a plurality of sets of slice data have been acquired during the first emission of the ultrasonic signal emission source 1, a second emission is performed by the ultrasonic signal emission source 1 to acquire information about portions of the object to be detected not acquired during the first emission. As shown in FIG. 2B, compared to the slices S11, S12 . . . S1N acquired during the first emission, a delay time is provided for each of the slices S21, S22 . . . S2N acquired during the second emission of the ultrasonic signal emission source 1 so as to acquire the information about the portions of the object to be detected not acquired during the first emission. Similarly, emissions are performed in turn until a space between every two adjacent slices acquired during the first emission, which corresponds to a reading time of a slice image, is fully filled with slices, as shown in FIG. 2B. As shown in FIG. 2B, respective sets of reflected echo signals relating to M*N slices are read separately, and then, information about these slices is integrated to acquire characteristics of the object to be detected, as shown in FIG. 2.

In other words, ultrasonic waves emitted by the ultrasonic signal emission source 1 travel along their propagation direction to pass through a thickness of the object to be detected; each section plane of the object to be detected through which the ultrasonic waves pass will reflect echo signals, the echo signals reflected by various section planes will be successively reflected back to the receiving array 2, and a predetermined reading time period must be provided to read the plurality of reflected echo signals received by the entire receiving array 2; therefore, if no timing control were performed, the receiving array 2 would continuously receive the echo signals reflected by various section planes during the emission of ultrasonic waves by the ultrasonic signal emission source 1, thereby making it impossible to acquire the needed information.

In the present disclosure, the receiving array 2 includes a plurality of ultrasonic signal receiving circuits arranged in an array, and each ultrasonic signal receiving circuit at least includes an ultrasonic receiver, which receives echo signals reflected onto it and may store and read these signals in order to record them for subsequent analysis processing.

In the present disclosure, the entire array of ultrasonic signal receiving circuits included in the receiving array 2 simultaneously receives and stores a set of reflected echo signals relating to a specific slice and then reads these signals row by row. In this process, the receiving array 2 reads all the reflected echo signals relating to the specific slice before a predetermined reading time period ends, without receiving echo signals reflected back to it. Thereafter, the receiving array 2 is turned on again to receive a set of reflected echo signals relating to the next slice. The predetermined reading time period is decided by a reading time of the reflected echo signals stored in the plurality of ultrasonic signal receiving circuits included in the receiving array 2. For example, in the present disclosure, a reading time of a slice image is equal to a reading time of the reflected echo signals stored in the plurality of rows of ultrasonic signal receiving circuits, that is, h/fgate, where fgate is a switching frequency of each gate line Gate (the reciprocal of fgate is a reading time of reflected echo signals stored in each row) and h is the number of rows.

Due to the time taken by the receiving array 2 to read a complete slice, during one emission of the ultrasonic signal emission source 1, the two sets of slice data successively received by the receiving array 2 reflect information about section planes of two slices spaced apart from one another in the object to be detected. In the present disclosure, a set of slices received by the receiving array 2 during one emission of the ultrasonic signal emission source 1 is referred to as a slice group, and accordingly, the set of slices received by the receiving array 2 during the first emission of the ultrasonic signal emission source 1 is referred to as a first slice group. Two adjacent slices in one slice group refer to slices received at two consecutive turn-on times of the receiving array 2 during one emission of the ultrasonic signal emission source 1. For example, as shown in FIG. 2B, the first slice group includes the slices S11 to S1N, in which S11 and S12 are two slices adjacent to each other; a time difference between respective times when the receiving array 2 receives the two adjacent slices is a reading time of a slice image.

As shown in FIG. 2B, the number of slices between two adjacent slices (for example, S11 and S12) in the first slice group is the number of emissions to be further made by the ultrasonic signal emission source 1, and accordingly, the number of slices between the two adjacent slices plus one is approximately the number of slice groups by which the object to be detected is divided. In other words, the number of slices by which the object 4 to be detected is divided is equal to the product of the number of slice groups and the number of slices in each slice group, that is, the total number of slices to be received by the receiving array 2 is equal to the product of the number of slice groups and the number of slices in each slice group.

Specifically, as described above, an ultrasonic imaging system includes the ultrasonic signal emission source 1 and the receiving array 2, which cooperate to define the detection region 3, and the edge interface of the detection region 3 distal to the receiving array 2 is the farthest interface 30.

After the ultrasonic signal emission source 1 is turned on to emit ultrasonic waves, the first set of slice data received by the receiving array 2 should reflect information about the surface of the detection region 3 (that is, the edge interface of the detection region 3 proximal to the receiving array 2). Therefore, after the first predetermined time period has elapsed since the ultrasonic signal emission source 1 started the first emission, the receiving array 2 is controlled to be turned on to acquire a set of reflected echo signals relating to the first slice in the first slice group, and this set of reflected echo signals is reflected by the surface of the detection region and represents information about this surface.

The receiving array 2 stores the set of reflected echo signals relating to the first slice upon reception thereof, and thereafter, reads the set of reflected echo signals received row by row, without receiving any reflected echo signals. Once the receiving array 2 finishes reading the set of reflected echo signals approximately reflecting characteristics of the surface of the detection region, it is reset and then turned on again to receive and store a set of reflected echo signals reflecting characteristic of the succeeding section plane of the detection region; thereafter, the receiving array 2 reads the set of the reflected echo signals relating to the this section plane row by row without receiving any reflected echo signals. The above process is repeated until the ultrasonic waves emitted by the ultrasonic signal emission source 1 travel beyond the farthest interface, and the farthest interface may be acquired by multiplying the velocity of the ultrasonic waves with a total reading time of a plurality of slice images.

The distance between the two slices respectively corresponding to the surface and the succeeding section plane of the detection region corresponds to the time difference between the two turn-on times of the receiving array 2, and both of them reflect the velocity of the ultrasonic waves and a time for the receiving array 2 to read a set of reflected echo signals relating to a complete slice.

As can be seen from the foregoing, due to the time difference between the two receiving or turn-on times of the receiving array 2, there is a certain distance between the surface and the succeeding section plane respectively corresponding to S11 and S12, and information about a portion between the surface and the succeeding section plane is not received, stored and read by the receiving array 2; therefore, the information about this portion is not acquired during this emission. This information will be acquired during the succeeding emissions of ultrasonic waves by the ultrasonic signal emission source 1.

As described above, the ultrasonic signal emission source 1 may be a specific type of emission source, for example, a point emission source. Ultrasonic waves emitted by the point emission source cover the surface of the object to be detected at the same time, and they then propagate along their propagation direction and pass through various parts of the object 4 to be detected along the depth-wise direction thereof. In the present disclosure, the number of slice groups and the number of slices in each slice groups to be received by the receiving array 2 may be determined by the wavelength $\lambda$ and the frequency f of the ultrasonic waves emitted by the ultrasonic signal emission source 1, the velocity of the ultrasonic waves v, a reading time of the reflected echo signals stored in each row of ultrasonic signal receiving circuits 1/fgate (that is, the reciprocal of the switching frequency of each gate line Gate fgate), the number of rows of ultrasonic signal receiving circuits h included in the receiving array 2, the number of slices N in a single wavelength (that is, the number of slices receivable by the receiving array during one emission of ultrasonic waves), the detection distance s (that is, the length of the detection region along its depth-wise direction, which is equal to the distance from the surface of detection region to the farthest interface thereof).

For example, in some embodiments of the present disclosure, the processes performed during the first emission of ultrasonic waves by the ultrasonic signal emission source 1 are to be described as follows:

after the first predetermined time period has elapsed since the ultrasonic signal emission source 1 was turned on for the first time, the receiving array 2 is turned on at a first time point t0 (equal to a time when the receiving array 2 is able to receive a set of reflected echo signals relating to the first slice in the first slice group) to receive and store an entire set of reflected echo signals relating to the first slice; thereafter, it reads these reflected echo signals stored in the plurality of ultrasonic signal receiving circuits included in the receiving array 2 row by row and stores them into a storage device, without receiving any reflected echo signals; it is to be noted that since the first predetermined time period is very short, the first slice typically reflects information about the surface of the detection region; and for the first emission, the ultrasonic signal emission source 1 and the receiving array 2 may be turned on at the same time; the first predetermined time period is less than or equal to a time length obtained by dividing the sum of the distance between the ultrasonic signal emission source 1 and the surface of the object to be detected and the distance between the surface and the receiving array 2 by the velocity of ultrasonic waves;

after the reading is completed, the receiving array 2 is reset and turned on again to receive and store a set of reflected echo signals relating to the second slice in the first slice group; thereafter, it reads these reflected echo signals stored in the plurality of ultrasonic signal receiving circuits included in the receiving array 2 row by row, without receiving any reflected echo signals; and the above process is repeated until the ultrasonic waves emitted by the ultrasonic signal emission source 1 for the first time travel beyond the farthest interface.

The processes performed during the second emission of ultrasonic waves by the ultrasonic signal emission source 1 are to be described as follows:

after the second predetermined time period has elapsed since the ultrasonic signal emission source 1 was turned on for the second time, the receiving array 2 is turned on at a second time point t1 (equal to a time when the receiving array 2 is able to receive a set of reflected echo signals relating to the first slice in the second slice group) to receive and store an entire set of reflected echo signals relating to the first slice in the second slice group, and as shown in FIG. 2B, the first slice in the second slice group should be located between the first slice S11 and the second slice S12 in the first slice group; thereafter, the receiving array 2 is caused to read these reflected echo signals row by row, without receiving any reflected echo signals; a time difference between the second time point t1 and the first time point t0 is a reading time of a slice image, and the second predetermined time period is longer than the first predetermined time period as a preceding predetermined time period by the length of the predetermined fine-tuning time, and a result of the length of the predetermined fine-tune time divided by two is greater than or equal to $v/f*N$ and less than a reading time of an image, where f is the frequency of the ultrasonic waves, N is the number of slices in a single wavelength, v is the velocity of the ultrasonic waves;

after the reading is completed, the receiving array 2 is reset and turned on again to receive and store a set of reflected echo signals relating to the second slice in the second slice group; thereafter, it reads these reflected echo signals row by row without receiving any reflected echo signals; and the above process is repeated until the ultrasonic signals emitted by the ultrasonic signal emission source 1 for the second time travel beyond the farthest interface.

Similarly, the ultrasonic signal emission source 1 emits ultrasonic waves for the third time, and then, the receiving array 2 receives a set of reflected echo signals relating to a first slice in a third slice group and so on; in this manner, emissions are performed in turn until a set of reflected echo signals relating to an $N^{th}$ slice in an $M^{th}$ slice group is received, stored and read by the receiving array 2 row by row.

In addition, in order to increase the detection accuracy without acquiring too much unnecessary data, prior to the detection, coarse scanning (that is, the ultrasonic signal emission source is turned on only a few times) may be performed to acquire preliminary information about the object to be detected in the detection region 3, for example, information about N slices acquired simply by one emission of the ultrasonic signal emission source 1; based on the information, the approximate location of the object to be detected in the detection region and the depth of the object to be detected along the propagation direction of the ultrasonic waves are determined, that is, a region of the object to be detected is determined; thereafter, the method described above is employed to perform fine scanning exclusively on the region of the object to be detected, that is, the region of the object to be detected thus determined is used as the detection region for the fine scanning, and the ultrasonic signal emission source 1 is turned on multiple times to generate more sets of slice data to be received by the receiving array 2 for analysis processing, thereby increasing the detection accuracy and speed.

Figure 3:
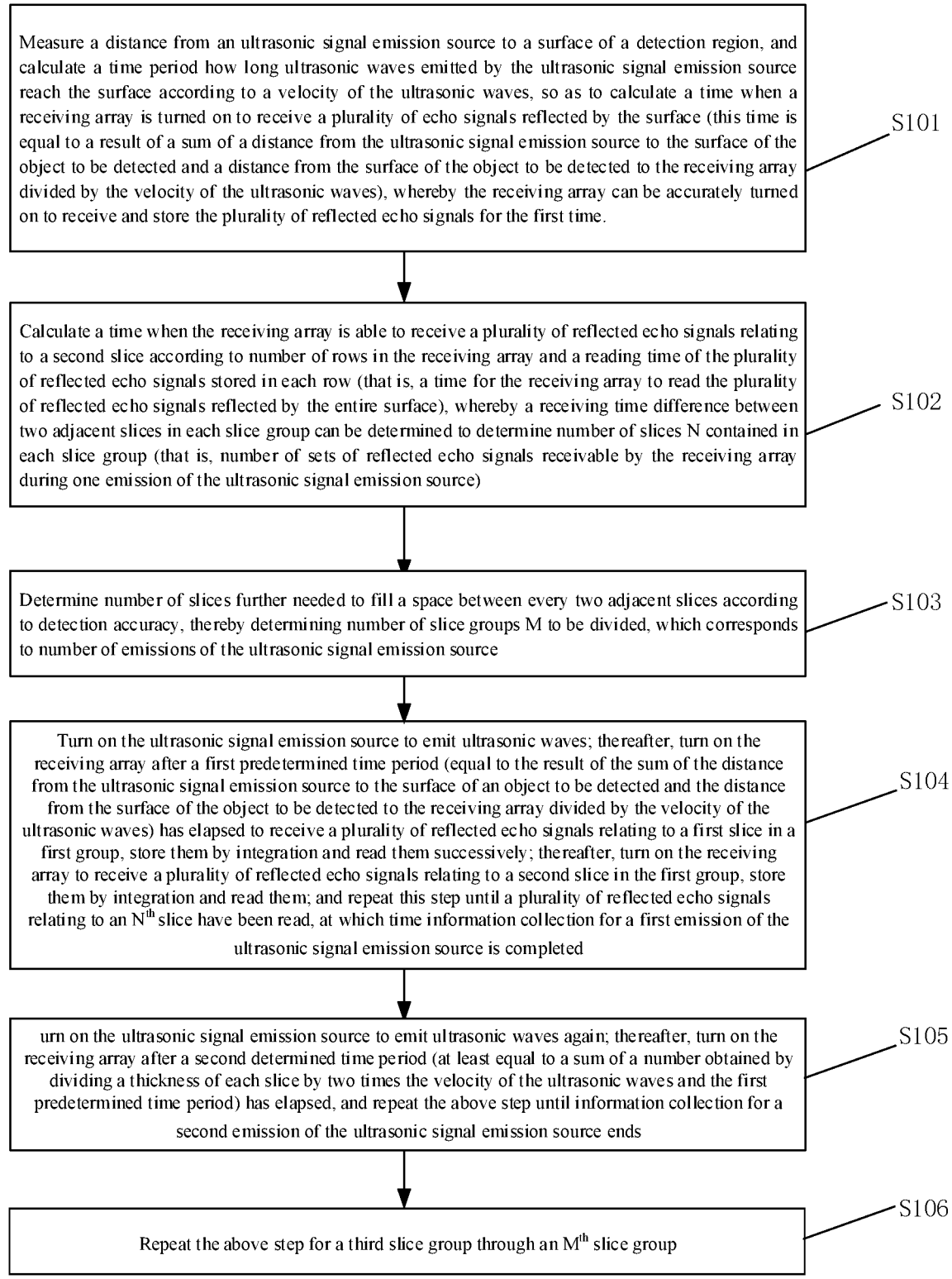
FIG. 3 is a flow chart of an imaging method of an ultrasonic imaging apparatus according to some embodiments of the present disclosure.

Specifically, as shown in FIG. 3, an imaging method of an ultrasonic imaging apparatus provided in the present disclosure includes the following steps S101 through S106:

S101: Measure a distance from an ultrasonic signal emission source to a surface of a detection region, and calculate a time period how long ultrasonic waves emitted by the ultrasonic signal emission source reach the surface according to a velocity of the ultrasonic waves, so as to calculate a time when a receiving array is turned on to receive a plurality of echo signals reflected by the surface (this time is equal to a result of a sum of a distance from the ultrasonic signal emission source to the surface of the object to be detected and a distance from the surface of the object to be detected to the receiving array divided by the velocity of the ultrasonic waves), whereby the receiving array can be accurately turned on to receive and store the plurality of reflected echo signals for the first time;

S102: Calculate a time when the receiving array is able to receive a plurality of reflected echo signals relating to a second slice according to number of rows in the receiving array and a reading time of the plurality of reflected echo signals stored in each row (that is, a time for the receiving array to read the plurality of reflected echo signals reflected by the entire surface), whereby a receiving time difference between two adjacent slices in each slice group can be determined to determine number of slices N contained in each slice group (that is, number of sets of reflected echo signals receivable by the receiving array during one emission of the ultrasonic signal emission source);

S103: Determine number of slices further needed to fill a space between every two adjacent slices according to detection accuracy, thereby determining number of slice groups M to be divided, which corresponds to number of emissions of the ultrasonic signal emission source;

Step 104: Turn on the ultrasonic signal emission source to emit ultrasonic waves; thereafter, turn on the receiving array after a first predetermined time period (equal to the result of the sum of the distance from the ultrasonic signal emission source to the surface of an object to be detected and the distance from the surface of the object to be detected to the receiving array divided by the velocity of the ultrasonic waves) has elapsed to receive a plurality of reflected echo signals relating to a first slice in a first group, store them by integration and read them successively; thereafter, turn on the receiving array to receive a plurality of reflected echo signals relating to a second slice in the first group, store them by integration and read them; and repeat this step until a plurality of reflected echo signals relating to an $N^{th}$ slice have been read, at which time information collection for a first emission of the ultrasonic signal emission source is completed;

S105: Turn on the ultrasonic signal emission source to emit ultrasonic waves again; thereafter, turn on the receiving array after a second determined time period (at least equal to a sum of a number obtained by dividing a thickness of each slice by two times the velocity of the ultrasonic waves and the first predetermined time period) has elapsed, and repeat the above step until information collection for a second emission of the ultrasonic signal emission source ends; and S106: Repeat the above step for a third slice group through an $M^{th}$ slice group.

In the above-described ultrasonic imaging method of the present disclosure, it is assumed that the detection region is divided into a plurality of slices in a three dimensional space, and these slices are correspondingly mapped to a plurality of reflected echo signals relating to a plurality of slices received by the receiving array 2. The receiving array 2 integrates the plurality of reflected echo signals relating to each slice every time it receives these signals, and for one emission of the ultrasonic signal emission source, a plurality of complete slice images can be collected, that is, a plurality of reflected echo signals relating to the plurality of slices are received by the receiving array 2. The plurality of complete slice images acquired after a plurality of emissions of the ultrasonic signal emission source are integrated to reproduce an image of the object to be detected in the detection region, thereby greatly increasing the transmission frame rate of image and enhancing the display effect while ensuring real-time performance.

The receiving array 2 of the present disclosure includes a plurality of ultrasonic signal receiving circuits 20 arranged in a plurality of rows and columns, each row of ultrasonic signal receiving circuits 20 is connected to a gate line Gate, each column of ultrasonic signal receiving circuits 20 is connected to a reading line Read, and signals read via the reading lines are transmitted through an analog-to-digital converter ADC to a processor for further integration processing.

Figure 5:
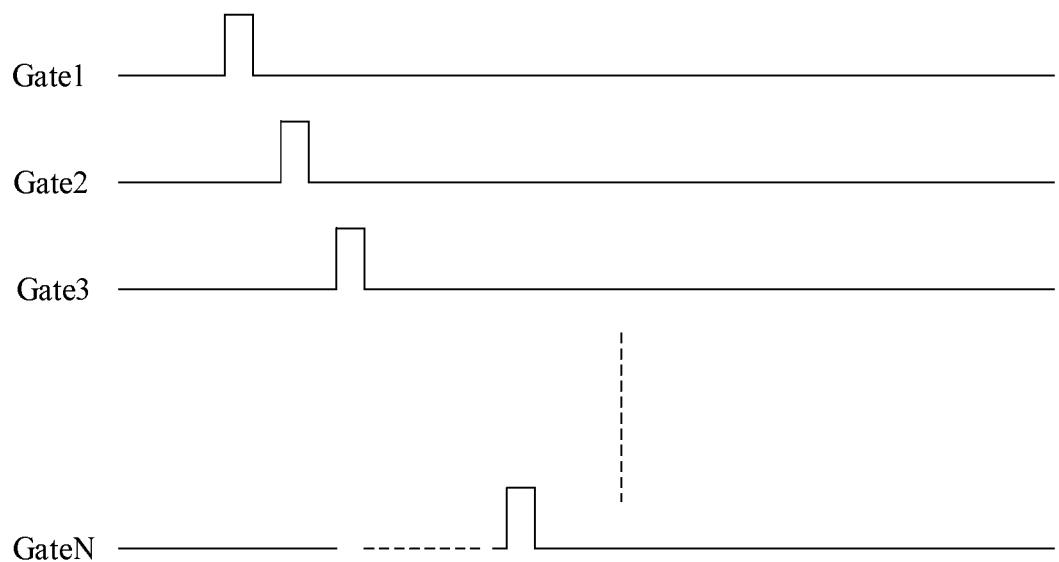
FIG. 5 is an operation timing diagram of a receiving array of an ultrasonic imaging apparatus according to some embodiments of the present disclosure.

In the present disclosure, a plurality of reflected echo signals received by the plurality of ultrasonic signal receiving circuits 20 in the receiving array 2 are successively read under the control of the plurality of gate lines Gate connected to these circuits. As shown in FIGS. 4 and 5, the plurality of gate lines Gate are turned on successively such that the plurality of reflected echo signals stored in the plurality of ultrasonic signal receiving circuits 20 are read successively.

Figure 6:
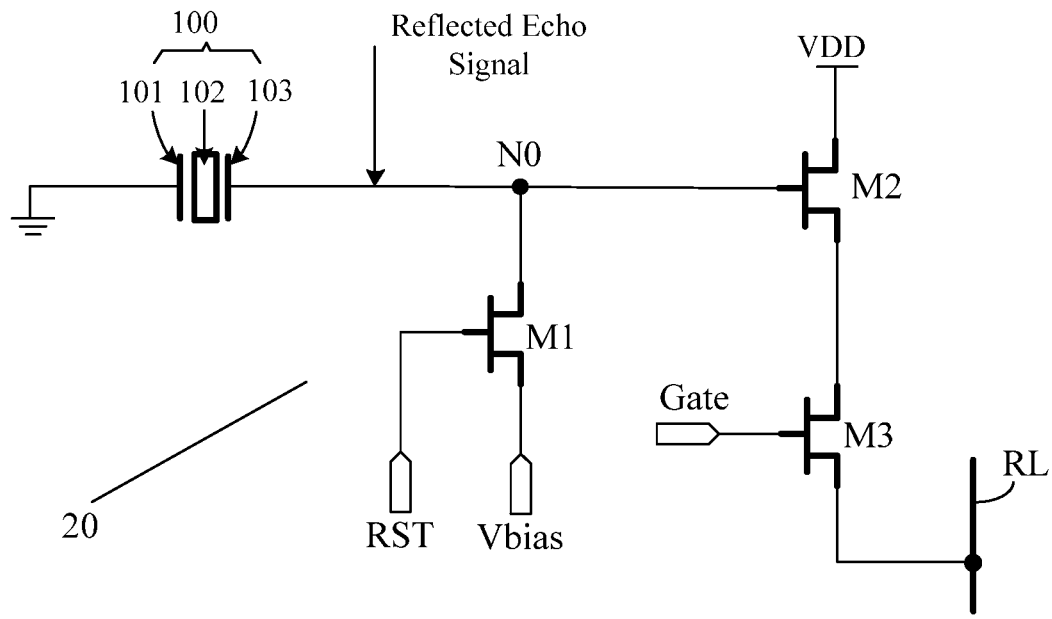
FIG. 6 is a schematic diagram of a configuration of an ultrasonic signal receiving circuit included in a receiving array of an ultrasonic imaging apparatus according to some embodiments of the present disclosure.

Specifically, as shown in FIG. 6, an ultrasonic signal receiving circuit 20 in some embodiments of the present disclosure includes an ultrasonic receiver 100, a first transistor M1, a second transistor M2 and a third transistor M3. The ultrasonic receiver 100 includes a driving electrode 101, a piezoelectric material layer 102 and a receiving electrode 103; the driving electrode 101 is connected to ground and the receiving electrode 103 is used to receive the reflected echo signals. The first transistor M1 includes a control electrode, a first electrode and a second electrode; the control electrode of the first transistor M1 is connected to a reset signal terminal RST, the first electrode thereof is connected to the receiving electrode 103, and the first electrode and the receiving electrode 103 both are connected to a node NO; the second electrode of the first transistor M1 is connected to a bias voltage terminal Vbias. The second transistor M2 includes a control electrode, a first electrode and a second electrode; the first electrode of the second transistor M2 is connected to a power supply voltage VDD, and the control electrode thereof is connected to the receiving electrode 103 and the node NO. The third transistor M3 includes a control electrode, a first electrode and a second electrode; the first electrode of the third transistor M3 is connected to the second electrode of the second transistor M2, the control electrode of the third transistor M3 is connected to a corresponding gate line Gate, and the second electrode of the third transistor M3 is connected to a corresponding reading line RL.

In the present disclosure, the first transistor M1, the second transistor M2 and the third transistor M3 may be field-effect transistors or MOS (metal-oxide-semiconductor) transistors. The ultrasonic receiver 100 may be a polyvinylidene difluoride (PVDF) piezoelectric transistor receiver, which receives a reflected echo signal, induces charges, and generates a piezoelectric signal in the form of a sine wave, as shown in FIG. 7.

Figure 7:
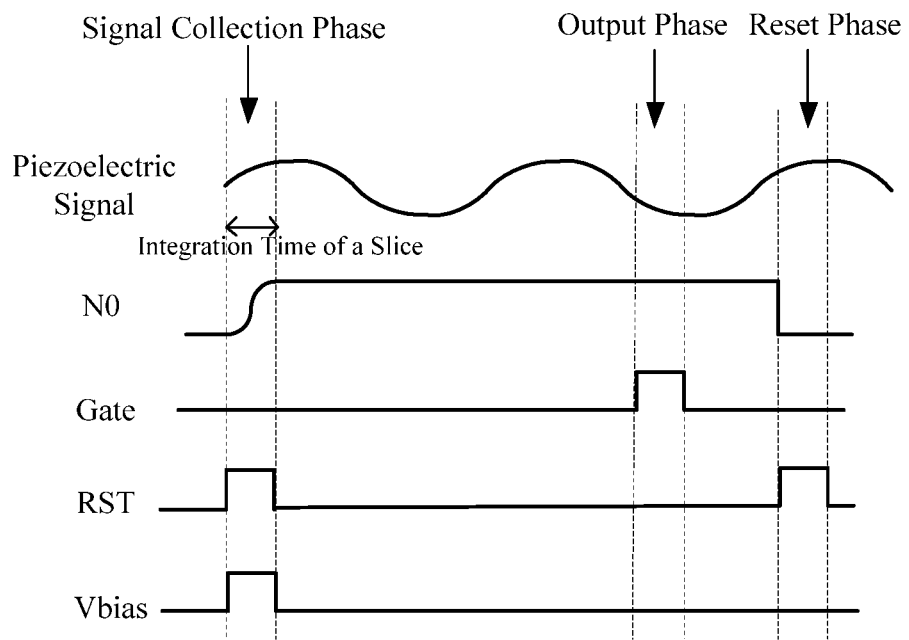
FIG. 7 is an operation timing diagram of the ultrasonic signal receiving circuit shown in FIG. 6.

A Vbias signal applied to the bias voltage terminal Vbias has two functions: one function is that a pulse width of the Vbias signal indicates an integration time for a reflected echo signal, that is, within a time period corresponding to the pulse width, the received reflected echo signal is integrated to acquire a signal at the node NO, as shown in FIG. 7; the other function is that the Vbias signal provides ground for the reset signal terminal RST to perform resetting, and as shown in FIG. 7, during the reset phase, a signal provided by the reset signal terminal RST is a high level signal, and the signal provided by the bias voltage terminal Vbias is a low level signal to reset the node NO for the next reception of the reflected echo signals.

Figure 8:
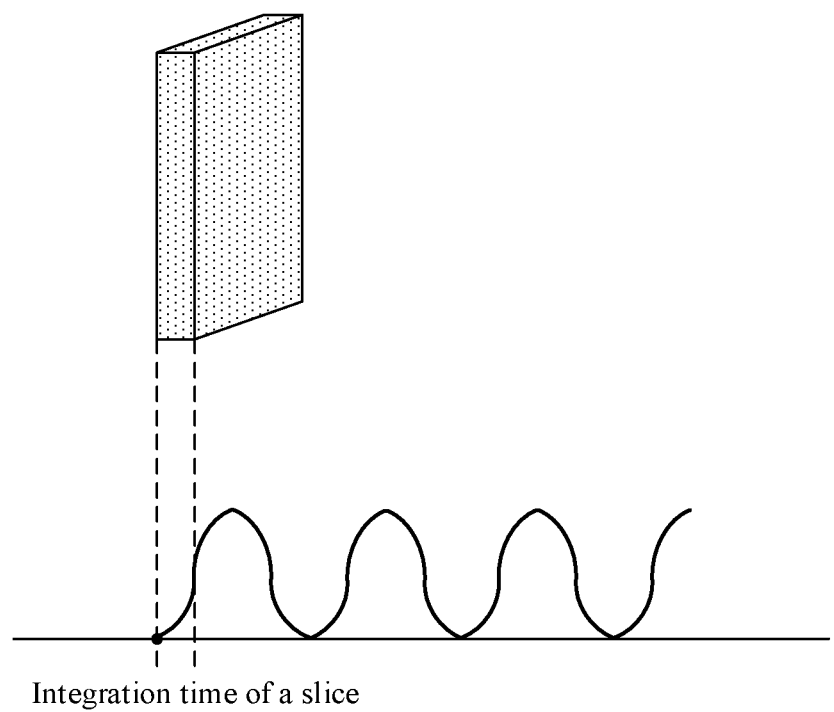
FIG. 8 is a schematic diagram of the integration of each slice by the ultrasonic signal receiving circuit shown in FIG. 7.

In addition, as shown in FIG. 8, the integration time is approximately equal to the thickness of a slice, that is, corresponds to a time difference between two turn-on times of the receiving array 2, and the shorter the integration time is, the higher the detection accuracy will be. However, as the thickness of a slice is getting smaller, more slices will be needed, and the number of emissions will increase.

The signal provided by the reset signal terminal Reset resets and discharges the ultrasonic signal receiving circuit once data of a frame has been read.

The function of a signal over the gate line Gate is to turn on the third transistor M3 and cause current outputted by the second transistor M2 (corresponding to the reflected echo signal received at the node NO) to flow to a back-end receiving circuit.

In one example, let f be the frequency of the ultrasonic waves emitted by the ultrasonic signal emission source 1, $\lambda$ the wavelength thereof, fgate the switching frequency of each gate line Gate (the reciprocal of fgate is a reading time of the reflected echo signals in each row), n the number of slices in a single wavelength (that is, the number of slices contained in each slice group, e.g., the number N as described above), h the number of rows of gate lines Gate (that is, the number of rows of ultrasonic signal receiving circuits in the receiving array 2), v the velocity of the ultrasonic waves, and s the detection distance (that is, the distance from the surface of the detection region to the farthest interface), then, 1) a reading time of a slice image=a reading time of the reflected echo signals stored in the plurality of rows of ultrasonic signal receiving circuits=1/fgate*h=h/fgate;
2) a transmission distance in the reading time of a slice image=the reading time of a slice image times the velocity of the ultrasonic waves=h*v/fgate;
3) number of slices to fill a space between two adjacent slice images=the transmission distance in the reading time of a slice image divided by a result of the wavelength divided by the number of slices in a single wavelength=h*v/fgate/(v/(f*n))=h*f*n/fgate, and the value thus obtained is an upper limit value, that is, maximum number, of slices to fill a space between two adjacent slice images; for example, in some cases, the number of slices to fill a space between two adjacent slice images may be reduced in order to save processing time, but this will lower the measurement accuracy;
4) a collecting time after each emission=a product of the detection distance times two divided by the velocity of the ultrasonic waves=2 s/v;

5) a collecting time of an entire three-dimensional image=the collecting time after each emission times the number of slices to fill a space between two adjacent slice images=2 s*h*f*n/(fgate*v); and
6) a frame rate=the reciprocal of the collecting time of an entire three-dimensional image=fgate*v/(2 s*h*f*n).

For example, in a case where the receiving array 2 includes ultrasonic signal receiving circuits 20 arranged in 100 rows and 100 columns, if f=5 MHz, T=200 ns, λ=0.3 mm, fgate=100 MHz, h=100, v=1500 m/s, s=25 cm, and the integration time=30 ns, then
1) n=200/30≈7
2) the collecting time of an entire three-dimensional image=0.25*2*100*5M*7/(100M*1500)≈11.66 ms; and
3) the frame rate=1/11.66 ms≈86 frames/second.

The frame rate obtained by the imaging method of the present disclosure is three times higher than the frame rate 30 frames/second in the related art.

To sum up, according to the ultrasonic imaging apparatus and the imaging method thereof provided in the present disclosure, the detection region of a three-dimensional space is divided into a plurality of slices; then, these slices are mapped onto a plurality of slices received by the receiving array; and a plurality of reflected echo signals relating to the plurality of the slices received by the receiving array are integrated to acquire information about the object to be detected in the entire detection region, wherein the plurality of ultrasonic signal receiving circuits included in the receiving array and arranged in an array are used to receive the plurality of reflected echo signals relating to each slice, each reflected echo signal is integrated by each ultrasonic signal receiving circuit acting as a pixel and then stored into a parasitic capacitor thereof, and the parasitic capacitor is reset after data stored therein has been read. The process of scanning slices according to the imaging method of the present disclosure is as follows: emitting ultrasonic waves for the first time; storing data of a complete slice and reading the data row by row; repeating data reading and storing for the succeeding complete slices in turn until the slice goes beyond the farthest interface; thereafter, emitting ultrasonic waves again, fine-tuning the position of a first slice during this emission such that it is located behind the first slice acquired during the preceding emission (that is, nearer to the farthest interface); and repeating the above steps until a space corresponding to a reading time of a slice image is filled with slices. According to the present disclosure, the detection region of the three-dimensional space is divided into slices and these slices are integrated, a plurality of complete slice images can be collected from one emission of ultrasonic waves, and the slice images acquired from a plurality of emissions are integrated to reproduce an image of the object to be detected, thereby greatly improving the frame rate of image and enhancing the display effect while ensuring the real time performance.

The foregoing descriptions of embodiments of the present disclosure have been presented for purposes of illustration and description, but they are not intended to be exhaustive or to limit the present disclosure to the precise forms or embodiments disclosed. Therefore, the foregoing descriptions are to be considered only as illustrative and not restrictive. Obviously, many modifications and variations will be apparent to a person skilled in the art. These embodiments were chosen and described to provide the best illustration of the principles of the present application in order to enable a person skilled in the art to understand various embodiments of the present disclosure and make various modifications as are suited to the particular use or implementation contemplated. It is intended that the present disclosure be limited only by the appending claims and the equivalents thereof.

The invention claimed is:

1. An imaging method of an ultrasonic imaging apparatus, wherein the ultrasonic imaging apparatus comprises an ultrasonic signal emission source and a receiving array that comprises a plurality of ultrasonic signal receiving circuits, both of which define a detection region; the detection region comprises a farthest interface, which is an edge interface of the detection region distal to the receiving array; the ultrasonic imaging apparatus is configured to detect an object to be detected in the detection region; and the imaging method comprises:

turning on the ultrasonic signal emission source to perform a first emission of ultrasonic waves toward the detection region and causing the ultrasonic waves to propagate through the detection region, a depth-wise direction of which is along a propagation direction of the ultrasonic waves, and thereafter, turning off the ultrasonic signal emission source; and turning on the receiving array at a first time point after a first predetermined time period having elapsed since the ultrasonic signal emission source was turned on, so as to simultaneously receive a plurality of reflected echoes returning from the detection region by the plurality of ultrasonic signal receiving circuits comprised in the receiving array; thereafter, causing the receiving array not to receive any reflected echoes, storing the plurality of reflected echoes by the plurality of ultrasonic signal receiving circuits, acquiring a plurality of reflected echo signals as a plurality of reflected echo signals relating to a first slice in the first emission, and reading the plurality of reflected echo signals relating to the first slice successively from the plurality of ultrasonic signal receiving circuits during a reading time period.

2. The imaging method according to claim 1, wherein after the reading the plurality of reflected echo signals successively, the imaging method further comprises: turning on the receiving array at a second time point to simultaneously receive a plurality of reflected echoes returning from the detection region by the plurality of ultrasonic signal receiving circuits comprised in the receiving array, and thereafter, causing the receiving array not to receive any reflected echoes, storing the plurality of reflected echoes by the plurality of ultrasonic signal receiving circuits, acquiring a plurality of reflected echo signals as a plurality of reflected echo signals relating to a second slice in the first emission, and reading the plurality of reflected echo signals relating to the second slice successively from the plurality of ultrasonic signal receiving circuits during a reading time period.

3. The imaging method according to claim 2, wherein
a time difference between the second time point and the first time point is a reading time of a slice image; and
the first predetermined time period is less than or equal to a time length obtained by dividing a sum of a distance between the ultrasonic signal emission source and a surface of the object to be detected and a distance between the surface of the object to be detected and the receiving array by a velocity of the ultrasonic waves.

4. The imaging method according to claim 3, wherein
after the reading the plurality of reflected echo signals successively, the receiving array is turned on again immediately; and after the reading the plurality of reflected echo signals received and relating to the second slice as a preceding slice successively, the imaging method further comprises:

step S1: turning on the receiving array again to simultaneously receive a plurality of reflected echoes returning from the detection region by the plurality of ultrasonic signal receiving circuits comprised in the receiving array, thereafter, storing the plurality of reflected echoes by the plurality of ultrasonic signal receiving circuits and acquiring a plurality of reflected echo signals as a plurality of reflected echo signals relating to a succeeding slice, and thereafter, reading the plurality of reflected echo signals relating to the succeeding slice successively from the plurality of ultrasonic signal receiving circuits during a reading time period; and step S2: repeating the step S1 until the succeeding slice goes beyond the farthest interface of the detection region, and after completing the step S2, acquiring number of turn-on times of the receiving array for the first emission of the ultrasonic signal emission source as number of slices N in a single wavelength.

5. The imaging method according to claim 4, wherein
a distance between the surface of the detection region and the farthest interface of the detection region is a detection distance s; and
when a product of the number of turn-on times of the receiving array and the reading time of the slice image is greater than the detection distance s, it is determined that a slice that has been received goes beyond the farthest interface of the detection region.

6. The imaging method according to claim 5, wherein after the succeeding slice going beyond the farthest interface of the detection region, the imaging method further comprises step S3: turning on the ultrasonic signal emission source again to perform another emission of ultrasonic waves toward the detection region and causing the ultrasonic waves to propagate through the detection region, the depth-wise direction of which is along the propagation direction of the ultrasonic waves, and thereafter, turning off the ultrasonic signal emission source;

turning on the receiving array after a second predetermined time period having elapsed since the ultrasonic signal emission source was turned on again, so as to simultaneously receive a plurality of reflected echoes returning from the detection region by the plurality of ultrasonic signal receiving circuits comprised in the receiving array; thereafter, causing the receiving array not to receive any reflected echoes, storing the plurality of reflected echoes by the plurality of ultrasonic signal receiving circuits, acquiring a plurality of reflected echo signals as a plurality of reflected echo signals relating to a first slice in the another emission, and successively reading the plurality of reflected echo signals relating to the first slice from the plurality of ultrasonic signal receiving circuits during a reading time period, wherein the second predetermined time period is longer than the first predetermined time period as a preceding predetermined time period by a predetermined fine-tuning time length.

7. The imaging method according to claim 6, wherein a result of the predetermined fine-tuning time length divided by two is greater than or equal to $v/f*N$ and less than the reading time of the slice image, where f is a frequency of the ultrasonic waves, N is the number of slices in a single wavelength and v is the velocity of the ultrasonic waves.

8. The imaging method according to claim 6, wherein
number of turn-on times of the ultrasonic signal emission source M is equal to one plus a result of the reading time of the slice image divided by the result of the predetermined fine-tuning time length divided by two.

9. The imaging method according to claim 8, further comprising: after the reading the plurality of reflected echo signals relating to the first slice in the another emission successively, turning on the receiving array again; and
performing the step S3, the step S1 and the step S2 successively.

10. The imaging method according to claim 9, further comprising: integrating the reflected echo signals that have been read to determine information about the object to be detected in the detection region.

11. An ultrasonic imaging apparatus of performing the imaging method according to claim 1, comprising:
an ultrasonic signal emission source emitting ultrasonic waves toward an object to be detected; and
a receiving array comprising a plurality of ultrasonic signal receiving circuits,
wherein the ultrasonic signal emission source and the receiving array define a detection region and a farthest interface of the detection region, such that the receiving array is configured to receive, store and read a plurality of reflected echo signals returning from the object to be detected in the detection region;
the ultrasonic signal emission source is a point emission source;
the receiving array and the ultrasonic signal emission source are on a first plane; and
a depth-wise direction of the detection region is orthogonal to the first plane.

12. The ultrasonic imaging apparatus according to claim 11, wherein the ultrasonic signal emission source is directly above the receiving array or on top of the receiving array.

13. The ultrasonic imaging apparatus according to claim 12, wherein the ultrasonic signal emission source is at a center of the receiving array.

14. The ultrasonic imaging apparatus according to claim 11, wherein an orthographic projection of the detection region on the receiving array falls within the receiving array.

15. The ultrasonic imaging apparatus according to claim 12, wherein
the plurality of ultrasonic signal receiving circuits are arranged in an array.

16. The ultrasonic imaging apparatus according to claim 15, further comprising a driving circuit, which is connected to the receiving array through a plurality of gate lines and a plurality of reading lines, wherein
each of the plurality of gate lines is connected to a row of ultrasonic signal receiving circuits to control the row of ultrasonic signal receiving circuits to be turned on; and
each of the plurality of reading lines is connected to a column of ultrasonic signal receiving circuits to read a plurality of reflected echo signals stored in the column of ultrasonic signal receiving circuits.

17. The ultrasonic imaging apparatus according to claim 16, wherein each of the plurality of ultrasonic signal receiving circuits comprises: an ultrasonic receiver, a first transistor, a second transistor and a third transistor, wherein
the ultrasonic receiver comprises a driving electrode, a piezoelectric material layer and a receiving electrode, the driving electrode is connected to ground, and the receiving electrode is used to receive the plurality of reflected echo signals;

the first transistor comprises a control electrode, a first electrode and a second electrode, the control electrode of the first transistor is connected to a reset signal terminal, the first electrode of the first transistor is connected to the receiving electrode, and the second electrode of the first transistor is connected to a bias voltage terminal;

the second transistor comprises a control electrode, a first electrode and a second electrode, the first electrode of the second transistor is connected to a power supply voltage, and the control electrode of the second transistor is connected to the receiving electrode; and the third transistor comprises a control electrode, a first electrode and a second electrode, the first electrode of the third transistor is connected to the second electrode of the second transistor, the control electrode of the third transistor is connected to a corresponding gate line, and the second electrode of the third transistor is connected to a corresponding reading line.

18. The imaging method according to claim 7, wherein number of turn-on times of the ultrasonic signal emission source M is equal to one plus a result of the reading time of the slice image divided by the result of the predetermined fine-tuning time length divided by two.

19. The imaging method according to claim 18, further comprising: after the reading the plurality of reflected echo signals relating to the first slice in the another emission successively, turning on the receiving array again; and performing the step S3, the step S1 and the step S2 successively.

20. The imaging method according to claim 19, further comprising: integrating the reflected echo signals that have been read to determine information about the object to be detected in the detection region.

* * * * *